United States Patent [19]

Cooper

[11] Patent Number: 5,135,683
[45] Date of Patent: Aug. 4, 1992

[54] PROCESS FOR PRODUCING A DEPROTECTED ALKOXYLATED POLYOL

[75] Inventor: Charles F. Cooper, Paoli, Pa.

[73] Assignees: Arco Chemical Technology, L.P., Wilmington, Del.; CPC International Inc., Englewood Cliffs, N.J.

[21] Appl. No.: 676,680

[22] Filed: Mar. 28, 1991

[51] Int. Cl.$^5$ ............................................. C09F 5/08
[52] U.S. Cl. ..................... 554/151; 560/189; 554/168; 554/172; 554/173; 568/623; 536/116; 536/120
[58] Field of Search ............... 260/410.6; 560/189

[56] References Cited

U.S. PATENT DOCUMENTS

| | | | |
|---|---|---|---|
| 2,610,125 | 9/1952 | Valko | 99/123 |
| 2,908,681 | 10/1959 | Anderson et al. | 260/234 |
| 3,337,595 | 8/1967 | Lamont et al. | 260/410.6 |
| 4,022,808 | 5/1977 | Yoshihara et al. | 260/410.6 |
| 4,115,415 | 9/1978 | Yoshihara et al. | 260/410 |
| 4,581,470 | 4/1986 | Hoy et al. | 560/189 |
| 4,849,242 | 7/1989 | Kershner | 426/601 |
| 4,861,613 | 8/1989 | White et al. | 426/611 |
| 4,983,329 | 1/1991 | Cooper | 260/410.7 |

FOREIGN PATENT DOCUMENTS

| | | |
|---|---|---|
| 043966 | 1/1982 | European Pat. Off. . |
| 415635 | 3/1991 | European Pat. Off. . |
| 415636 | 3/1991 | European Pat. Off. . |
| 207070 | 2/1984 | German Democratic Rep. . |
| 55-79313 | 6/1980 | Japan . |

*Primary Examiner*—Jose G. Dees
*Assistant Examiner*—Deborah D. Carr
*Attorney, Agent, or Firm*—Stephen D. Harper

[57] ABSTRACT

An improved process for the hydrolysis and purification of an alkoxylated polyol containing a ketal protective functionality is described. The process may be employed to prepare reduced calorie esterified alkoxylated polyol fat mimetics useful in cooking and in food compositions.

20 Claims, No Drawings

PROCESS FOR PRODUCING A DEPROTECTED ALKOXYLATED POLYOL

FIELD OF THE INVENTION

This invention pertains to methods for the preparation of deprotected alkoxylated polyols useful as synthetic intermediates in the production of esterified alkoxylated polyol fat substitutes. The invention additionally relates to processes whereby a protected alkoxylated polyol having a ketal protective functionality is hydrolyzed and the hydrolysis product thereafter is recovered in purified form from the aqueous reaction mixture.

BACKGROUND OF THE INVENTION

Esterified alkoxylated glycerin and other esterified alkoxylated polyols have recently been identified as useful reduced calorie fat substitutes. Compounds of this type, which are described more fully in U.S. Pat. Nos. 4,861,613 and 4,983,329, are substantially resistant to hydrolysis upon digestion owing to the high proportion of linkages in which the carbons adjacent to oxygen in the fatty acid ester groups are secondary or tertiary in structure. In a preferred embodiment of such substances, the structure may be represented as follows:

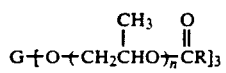

wherein G is a glyceryl radical, n is from about 1 to 3 on average, and R is a long chain paraffinic or olefinic hydrocarbon radical derived from a fatty acid.

However, the ability to use esterified alkoxylated polyols of this type at relatively high concentrations in food compositions is somewhat limited by the pronounced resistance of such substances to digestion. Since the esterified alkoxylated polyols are hydrolyzed and absorbed to only a very limited degree, they tend to retain their oil-like physical characteristics after ingestion. Consumption of large amounts of the fat substitutes can result in short bowel transit times and undesired laxative effects.

To enhance the acceptability of fat substitutes of this type, modified esterified alkoxylated glycerins have been developed which are somewhat less resistant to enzymatic hydrolysis than previously known esterified alkoxylated glycerins and yet still have significantly reduced calorie availability as compared to a conventional fully digestible triglyceride lipid. These modified esterified alkoxylated glycerins have one or two fatty acid ester groups attached directly to the carbons of the glyceryl radical. These directly attached ester groups are fairly readily hydrolyzed upon ingestion, rendering the compounds less fat-like in character owing to the loss of one or more long-chain fatty acid groups.

The ester groups in the esterified alkoxylated glycerin which are attached to the glyceryl radical through polyoxypropylene segments are resistant towards enzymatic hydrolysis. The structures of two preferred embodiments of such modified esterified alkoxylated polyols are as follows:

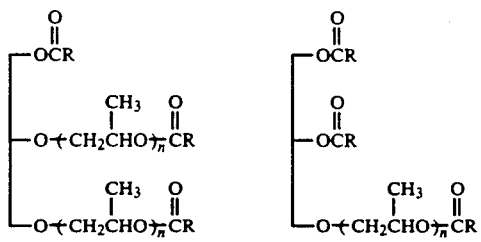

wherein R is a long-chain hydrocarbon radical derived from fatty acid.

The synthesis of esterified alkoxylated mono- or diglycerides of this type is not straightforward. Esterified propoxylated glycerin may be prepared by reacting glycerin with propylene oxide in the presence of a basic alkali metal catalyst to form a propoxylated glycerin. The propoxylated glycerin is then esterified with a fatty acid compound such as a free fatty acid, fatty acid ester, or fatty acid halide. Using this synthetic approach, however, it is not possible to have an ester group attached directly to the glyceryl residue since the propylene oxide tends to add in a random fashion to all three hydroxyl groups of the starting glycerin:

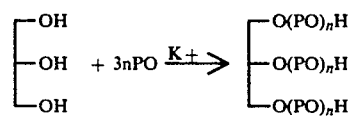

A possible alternative method of preparation of an esterified alkoxylated monoglyceride would be to propoxylate a fatty acid monoglyceride and then esterify the secondary hydroxyl groups of the propoxylated monoglyceride:

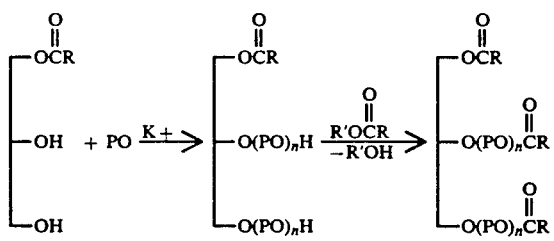

However, when this procedure is attempted, the product obtained is similar to the esterified propoxylated glycerin known in the prior art wherein oxypropylene units are present between the glyceryl radical and all three of the ester groups. Apparently, transesterification readily takes place under the reaction conditions necessary to achieve propoxylation of the fatty acid monoglyceride:

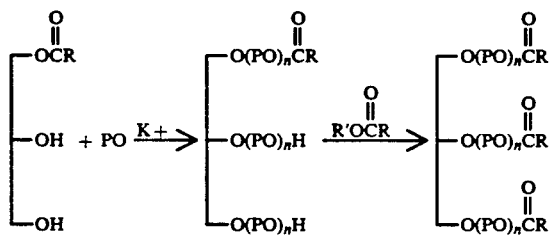

Thus, it is apparent there is a great need for processes whereby an esterified alkoxylated polyol having at least one ester group attached directly to the polyol residue may be readily prepared. The use of a ketal or acetal protective group to "mask" or "block" one or more hydroxyl groups is a commonly employed synthetic method in organic chemistry. Since a ketal or acetal group is normally nonreactive under basic conditions, other functional groups in an organic compound having such a protective group may be readily transformed using a basic reagent while not disturbing the ketal or acetal. The protective group may then be removed by acid-catalyzed hydrolysis and the free hydroxyl group(s) thereby generated subsequently further reacted in any desired manner.

This synthetic approach was employed in U.S. Pat. No. 4,581,470 to prepare 1,2- and 1,3-extender polyols useful in polyurethane formulations. The reference indicates, for example, that a starter such as glycerin may be reacted with a blocking agent such as acetone to form a blocked triol starter derivative (e.g., isopropylidene glycerin, which may also be referred to as 2,2-dimethyl-1,3-dioxolane-4-methanol). The remaining free hydroxyl group is subsequently reacted with an alkylene oxide such as propylene oxide. The alkoxylated product thereby obtained is then treated with an aqueous acidic solution to hydrolyze the ketal functional group and unblock the protected hydroxyl groups. It may be readily seen that the deprotected alkoxylated glycerin thereby obtained could be esterified with a fatty acid or fatty acid derivative to yield a modified esterified alkoxylated glycerin fat substitute of the type described hereinabove. This reaction scheme may be illustrated as follows:

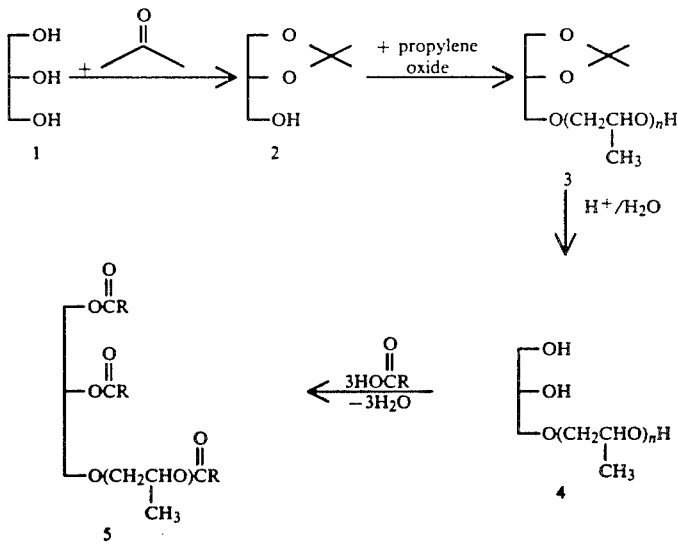

However, a multi-step process of this type will not be commercially attractive unless the individual steps involved can be simplified and streamlined as much as possible. The hydrolysis step, wherein protected alkoxylated polyol 3 is transformed to deprotected alkoxylated polyol 4, is particularly problematic since it involves an acid and substantial amounts of water, both of which must eventually be separated from the deprotected alkoxylated polyol or any subsequent ultimate product. Alkoxylated intermediates such as 3 or 4, by analogy to conventional polyether polyols such as polypropylene glycol or polyethylene glycol, would be expected to either have high water solubilities or a tendency to form emulsions in water. Additionally, as n is increased, the viscosity of such intermediates tends to increase thereby requiring the use of organic solvents. Subsequent complete removal of organic solvent will be necessary if the final esterified alkoxylated polyol is to be safely used as a fat substitute in food compositions.

In U.S. Pat. No. 4,581,470, the hydrolysis step is accomplished by treating the ketal-containing alkoxylated intermediate with aqueous sulfuric acid at an elevated temperature (110° C.) while simultaneously removing a portion of the water by distillation. The hydrolyzed product was then neutralized with aqueous potassium hydroxide and then stripped under high vacuum to remove the remaining water. The crude product required further treatment with magnesium silicate to remove the salts formed during neutralization. It may thus be seen that hydrolysis required at least four discrete steps. The overall process was consequently fairly lengthy and tedious since it involved removal of all the water present by distillation as well as a prolonged treatment to remove salts.

From the foregoing discussion, there is clearly a need for an improved and simplified process wherein a ketal protective group may be readily and conveniently removed from a protected alkoxylated polyol.

SUMMARY OF THE INVENTION:

This invention provides a process for producing a deprotected alkoxylated polyol comprising the steps of
(a) contacting an admixture of water and a protected alkoxylated polyol having a ketal protective functionality with a catalytically effective amount of an acid under conditions effective to hydrolyze the ketal protective functionality thereby forming a deprotected alkoxylated polyol;
(b) adding a base to the admixture so as to neutralize the acid and to cause the admixture to form a first and second phase wherein the water is predominantly contained in said first phase and the deprotected alkoxylated polyol is predominantly contained in said second phase; and (c) separating the second phase containing the desired deprotected alkoxylated polyol from the first phase.

The invention also provides a process for producing an esterified alkoxylated polyol comprising the steps of
(a) reacting a protected polyol having at least one free hydroxyl group and a ketal protective functionality with an epoxide in the presence of a catalytically effective amount of a basic alkoxylation catalyst under conditions effective to form a protected alkoxylated polyol wherein the ketal protective functionality remains intact;
(b) contacting an admixture of the protected alkoxylated polyol and water with a catalytically effective amount of an acid under conditions effective to hydrolyze the ketal protective functionality thereby forming a deprotected alkoxylated polyol;
(c) adding a base to the admixture so as to neutralize the acid and to cause the admixture to form a first and second phase wherein the water is predominantly contained in said phase and the deprotected alkoxylated polyol is predominantly contained in said second phase;
(d) separating the second phase containing the deprotected alkoxylated polyol from the first phase;
(e) reacting the deprotected alkoxylated polyol with a fatty acid moiety selected from the group consisting of free fatty acids, fatty acid esters, and fatty acid halides to form the desired esterified alkoxylated polyol.

DETAILED DESCRIPTION OF THE INVENTION:

Protected alkoxylated polyols having ketal protective functionalities which are suitable for use in the process of this invention may be prepared by any method known in the art. In general, the protected alkoxylated polyols are obtained by selecting a suitable polyol starter having at least two hydroxyl groups, blocking at least one (but not all) of the hydroxyl groups using a ketal protective group, and then alkoxylating the remaining free hydroxyl group(s) by reacting with an epoxide or mixture of epoxides. Preferably, the polyol starter has at least three hydroxyl groups, two of which are blocked using a cyclic ketal protective group. The two blocked hydroxyl groups are preferably separated by two or three carbon atoms.

The polyol starter, for example, may be a diol, triol, tetrol, pentol, hexol, heptol, octol or other such organic compound having at least two hydroxyl groups. Preferably, the hydroxyl groups are primary or secondary in structure and are bonded to aliphatic carbons. Readily available polyol starters suitable for use include, but are not limited to, glycols, glycerin, sugar alcohols, sugars, and the like. Polymeric or oligomeric polyol starters such as polyglycerol and polyvinyl alcohol can also be employed, if desired. Illustrative examples of polyol starters are as follows:

Diols ethylene glycol
diethylene glycol
triethylene glycol
propylene glycol
dipropylene glycol
tripropylene glycol
1,3-propanediol
2-methyl-1,3-propanediol
2,2-dimethyl-1,3-propanediol (neopentyl glycol)
1,4-butanediol
2,3-butanediol
1,3-butanediol
1,5-pentanediol
1,6-hexanediol
cyclohexanedimethanol

Triols glycerin
trimethylol propane
trimethylol ethane
trihydroxy hexane
trihydroxy butane
trihydroxy pentane
erythrose

Tetrols erythritol
pentaerythritol
threitol
ribose
arabinose
xylose
lyxose

Pentols ribitol (adonitol)
arabitol
xylitol
allose
altrose
glucose
mannose
gulose
idose
galactose
talose
fructose

Hexols dulcitol
iditol
mannitol
sorbitol

Heptols perseitol

Octols sucrose
maltose
lactose

As used herein, the term "ketal" signifies both acetal and ketal type functional groups. That is, the ketal protective functionality may be derived from either an aldehyde or a ketone. In a preferred embodiment of this invention, the ketal protective functionality has the general structure

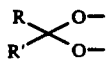

wherein R and R' are the same or different and are independently selected from the group consisting of hydrogen, alkyl, aryl, and aralkyl. This type of ketal protective functionality is particularly well-adapted for simultaneously blocking two hydroxyl groups on the polyol starter, especially hydroxyl groups separated by two or three carbon atoms. Examples of suitable alkyl groups include methyl, ethyl, propyl, isopropyl, butyl, isobutyl, sec-butyl, t-butyl, pentyl, as well as other $C_1$-$C_{12}$ aliphatic radicals. R or R' may alternatively be aryl groups such as phenyl or substituted phenyl. Illustrative aralkyl groups include benzyl, phenethyl, and the like. R and R' may also be covalently linked together as in a cyclohexyl, cycloheptyl or cyclopentyl structure. The choice of substituents R and R' is not critical for the successful operation of the process of this invention. Since the ketone or aldehyde which will be liberated upon hydrolysis of the protected alkoxylated polyol will need to be separated from the deprotected alkoxylated polyol produced, however, it is preferred that R and R' be hydrogen, methyl, or ethyl since the resulting aldehyde or ketone derived therefrom will be relatively volatile and highly soluble in water. The aldehyde or ketone can thus be readily removed by distillation or by extraction into the aqueous phase. Most preferably, R and R' are both methyl, as the resulting isopropylidene protecting group is highly stable under basic conditions but very labile under comparatively mild conditions of acidic hydrolysis.

Other types of ketal protective functionalities may also be used, however. For example, if it is desired to block only one hydroxyl group of the polyol starter, a vinyl ether such as 3,4-dihydropyran, 2,3-dihydrofuran or ethyl vinyl ether can be utilized to advantage.

Methods for the preparation of protected alkoxylated polyols of the type herein described are well-known in the art. For example, two contiguous hydroxyl groups may be condensed with an aldehyde or ketone using an acidic catalyst to produce a cyclic ketal functionality. Suitable aldehydes include, but are not limited to, formaldehyde, acetaldehyde, n-butyraldehyde, isobutyraldehyde, n-valeraldehyde, isovaleraldehyde, n-caproaldehyde, n-heptaldehyde, acrolein, crotonaldehyde, benzaldehyde, furfural and the like. Illustrative ketones include acetone, methylethyl ketone, methylpropyl ketone, diethyl ketone, hexanone, methylisobutyl ketone, dipropyl ketone, diisoproyl ketone, di-n-butyl ketone, diisobutyl ketone, chloroacetone, dichloroacetone, cyclohexanone, phorone, benzophenone, and acetophenone. Azeotropic distillation or a dehydrating agent can be employed to remove the water generated and to drive the reaction to completion. An acetal exchange reaction using a reagent such as 2,2-diethoxypropane is an alternative synthetic approach. Appropriate methods are described in S. Patai *The Chemistry of the Hydroxyl Group*, Part 2, Chapter 18, Interscience Publishers (1971), F. A Corey et al. *Advanced Organic Chemistry, Part B-Reactions and Synthesis*, Plenum Press, pp, 408-414 (1977), C. B. Reese, *Protective Groups in Organic Chemistry*, pp. 104-108, 121-130, and references cited therein.

Illustrative protected polyols preferred for use in the process of this invention include 2,2-dimethyl-4-hydroxymethyl-1,3-dioxolane, 2,2-dimethyl-5-ethyl-5-hydroxymethyl-1,3-dioxane, and 2,2-dimethyl-5,5-dihydroxy methyl-1,3-dioxane.

The protected alkoxylated polyol is obtained by reacting the protected polyol with one or more epoxides using any suitable alkoxylation technique. Methods for alkoxylating organic compounds containing hydroxyl groups are well known in the art, as illustrated, for example in the teachings of U.S. Pat. No. 4,581,470 and European Pat. Application 043,966. The reaction conditions selected are such that the ketal protective functionality remains intact during alkoxylation. Due to the stability of the ketal protective functionality in a basic environment, it is advantageous to employ a basic catalyst to promote the epoxide reaction.

The basic catalyst is preferably be selected from the group consisting of basic alkali metal compounds, basic alkaline earth compounds, and basic tertiary amines. Suitable alkali metal and alkaline earth catalysts include the hydrides, carbonates, oxides, hydroxides, carboxylates, alkoxides, and sulfates of lithium, sodium, potassium, barium, calcium, and strontium as well as the elemental forms of the metals (e.g., sodium or potassium metal dispersions). Generally speaking, it is desirable to pre-react the protected polyol with the alkali metal or alkaline earth catalyst to form the salt of the protected polyol prior to reaction with the epoxide. For example, if sodium hydroxide or potassium hydroxide is employed as the catalyst, a mixture of the protected polyol and catalyst may be heated under conditions such that the water formed by reaction of the components is removed and the alkali metal salt of the protected polyol is formed.

Suitable tertiary amines for use in this process include aliphatic, aromatic, and mixed aliphatic-aromatic amines such as triethylamine, N,N-dialkyl anilines, dimethylaminocyclohexane, tri-n-propylamine, tetraethyl ethylenediamine, N,N'-dialkylpiperazines, N-alkylpiperidines, pyridine and substituted pyridines, N-alkyl pyrrolidinones, quinuclidine, and the like.

The amount of basic catalyst employed should be sufficient to effectively catalyze the addition of the epoxide to the hydroxyl group(s) of the protected polyol. Preferably this amount is from about 0.01 to 1 equivalent of basic catalyst per equivalent of hydroxyl groups in the protected polyol. The epoxide and protected polyol are preferably reacted at a temperature of from about 50° C. to 175° C. for a time effective to accomplish substantial (e.g., over 75%) conversion of the epoxide. Reaction times of from 1 to 48 hours will typically suffice. The molar ratio of epoxide to protected polyol may be varied as desired depending upon the degree of alkoxylation desired in the final deprotected alkoxylated polyol, but generally from about 1 to 25 equivalents of epoxide per equivalent of hydroxyl groups in the protected polyol will be typically employed. It is generally desirable to add the epoxide incrementally with agitation to the protected polyol and basic catalyst. The alkoxylation may be carried out in the presence of an inert organic solvent. When the desired degree of epoxide conversion has been achieved, the protected alkoxylated polyol may be purified by removing any unreacted epoxide by a suitable method such as vacuum stripping. The protected alkoxylated polyol may also be treated to remove the residual basic catalyst. Methods such as filtration, extraction, precipitation, or absorption can be used depending on the particular catalyst employed. Any of the standard methods for removing a basic catalyst from an alkoxylated product may be employed. If an alkali metal or alkaline earth catalyst is present, for example, a particularly advantageous method of catalyst removal involves heating the product with magnesium silicate to absorb the metal and then filtering to remove the magnesium silicate. However, catalyst removal at this step is not required since an excess of acid may simply be employed in the subsequent hydrolysis step in order to both neutralize the basic alkoxylation catalyst and to provide an acidic environment for removal of the ketal protective functionality.

The epoxide to be reacted in the alkoxylation step with the protected polyol may be any organic compound containing an oxiranyl functionality, but preferably is a $C_2$-$C_6$ aliphatic epoxide. Propylene oxide is the most preferred epoxide, but other suitable $C_2$-$C_6$ aliphatic epoxides include ethylene oxide, 1,2-butene oxide, isobutylene oxide, 2,3-butene oxide, 1,2-pentene oxide, 2,3-pentene oxide, cyclopentene oxide, 1,2-hexene oxide, cyclohexene oxide and the like. Other epoxides such as epichlorohydrin, 1-octene oxide, allyl glycidyl ether, phenyl glycidyl ether, phenyl glycidyl ether, styrene oxide, butadiene mono-oxide, and the like may also be used, however. Mixtures of epoxides may be employed. If more than one epoxide is used, it may be desirable to add the different epoxides sequentially so as to vary the location of the different oxyalkylene repeating units within the end product. Ethylene oxide, if used in combination with propylene oxide, should not constitute more than about 25 mole percent of the total amount of epoxide since higher amounts will tend to make the resulting protected alkoxylated polyol more hydrophilic and interfere with the phase separation process which takes place during the process of this invention. For these reasons, the carbon:oxygen molar ratio in the oxyalkylene segment of the protected alkoxylated polyol is preferably at least about 2.75:1.

In a preferred embodiment of this invention, the protected alkoxylated polyol is a protected propoxylated glycerin having the general structure

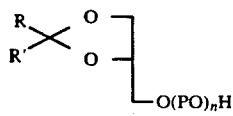

wherein R and R' are the same or different and are independently selected from the group consisting of hydrogen, methyl, and ethyl, PO is an oxypropylene unit (i.e.,

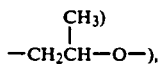

and n is from about 2 to 15 on average.

The protected alkoxylated polyol is treated with water and a catalytically effective amount of an acid under conditions effective to hydrolyze the ketal protective functionality thereby forming a deprotected alkoxylated polyol. The amount of water may vary, but preferably the weight ratio of water to protected alkoxylated polyol is from about 0.1:1 to about 2:1. Most preferably, the weight ratio is from about 0.5:1 to about 1.5:1. The optimum amount of water will be influenced by the relative hydrophobicity of the deprotected alkoxylated polyol. A deprotected alkoxylated polyol containing 1-pentene oxide epoxide units, for example, will be more hydrophobic than a deprotected alkoxylated polyol containing ethylene oxide and propylene oxide epoxide units and consequently will require less water to achieve a well-defined phase separation in the subsequent neutralization step. The admixture of water and protected alkoxylated polyol is preferably homogeneous while acid treatment is being performed in order that hydrolysis may proceed at a optimum rate.

The acid used may be any protic acid having a pka sufficiently low so as to effectively catalyze the hydrolysis of the protective ketal functionality. In general, the acid should have a pka of less than about 3 and more preferably has a pka of less than about 2. Although an organic acid such as chloroacetic acid, p-toluene sulfonic acid, oxalic acid or the like may be employed, it is preferred to use a mineral acid such as hydrochloric acid, nitric acid, sulfuric acid, phosphoric acid, phosphorous acid, or the like. A strongly acidic ion exchange resin such as "AMBERLYST 15" or similar polymeric resin containing pendent sulfonic acid groups would also be suitable. Preferably, however, the acid is water-soluble. The amount of acid is not critical, provided it is sufficient to catalyze the hydrolysis reaction within the desired contact time. Typically, if a mineral acid is used, the concentration of acid relative to the water present is advantageously from about 0.01 to 1 N. It will generally be desirable to combine the acid with the water before combining these reactants with the protected alkoxylated polyol. Alternatively, however, the water and protected alkoxylated polyol are first combined and then treated with the acid. The time required for complete hydrolysis of the ketal protective functionality will vary depending upon the structure of the ketal protective functionality, the reaction temperature, and the pka and concentration of the acid, among other factors, but generally will be from about 1 minute to 90 minutes. The hydrolysis is preferably carried out at a temperature of from about 10° C. to 75° C. Although higher temperatures may be used, they are not generally necessary due to the susceptibility of the ketal functionality towards hydrolysis. The hydrolysis step will yield both a ketone or aldehyde derived from the ketal protective functionality as well as the deprotected alkoxylated polyol having at least one hydroxyl group more than the protected alkoxylated polyol starting material.

Following the hydrolysis step, a base is combined with the admixture of water and deprotected alkoxylated polyol so as to neutralize the acid and to cause the admixture to form a first and second phase. The water will be predominantly contained in the first phase while the deprotected alkoxylated polyol will be predominantly contained in the second phase. In addition, the salts formed by neutralization of the acid will be predominantly Contained in the aqueous phase. The process of this invention thus may be seen to provide a more convenient method for separating a deprotected alkoxylated polyol from a hydrolysis reaction mixture than the procedures described in the prior art. The base should have a pka sufficiently high to neutralize the acid used. In general, the base should have a pka of greater than about 11 and more preferably has a pka of greater than about 12. Although organic bases such as amines may be employed, it is preferred to use an inorganic base selected from the group consisting of ammonium hydroxide, alkali metal oxides, alkali metal hydroxides, alkaline earth oxides, alkaline earth hydroxides, and mixtures thereof. For reasons of cost and availability, sodium hydroxide and potassium hydroxide are especially preferred. Such bases are particularly useful if a strong mineral acid is employed in the hydrolysis step. Other inorganic bases such as alkali metal carbonates, bicarbonates, and phosphates can also be employed. Sufficient base is combined with the admixture of water and deprotected alkoxylated polyol so as to completely neutralize the acid present. The pH of the resulting mixture is optimally between about 6 and 8 and most preferably is about 7.

The addition of the base not only neutralizes the acid present but also causes the admixture to clearly separate into two phases. This phase separation was unexpected in view of the generally high solubility of conventional low molecular weight polyether polyols such as polypropylene glycol and polyethylene glycol in water and the absence of any organic solvent in the process. Without wishing to be bound by theory, it is believed that the phase separation is attributable to the unique structure and geometry of the deprotected alkoxylated polyols and the formation of salts during the neutralization step. The presence of the salts in the admixture is thought to enhance the separation between the aqueous and organic phases through a "salting-out" effect.

The base is preferably water-soluble and may be either combined directly with the water/deprotected alkoxylated polyol admixture or diluted first with additional water. If the base is diluted with water, the amount of water present in the prior hydrolysis step should be adjusted accordingly so that the total amount of water does not exceed the amount required to accomplish effective phase separation during neutralization. The temperature at which the neutralization is performed is not critical; generally, temperatures of from about 20° C. to 50° C. will be suitable. The base need only be in contact with the reaction mixture for a period of time sufficient to substantially neutralize the acid and to effect phase separation. Typically, this will be from about 1 minute to 60 minutes. It is preferred that the reaction mixture be agitated or stirred during addition of the base.

It is possible to further enhance the separation between the organic phase and aqueous process by incorporating a non-polar water-immiscible organic solvent into the mixture. Suitable solvents include, for example, aliphatic hydrocarbons (e.g., hexane, petroleum ether), aromatic hydrocarbons (e.g., benzene, toluene, xylene), halogenated hydrocarbons (e.g., chloroform, methylene chloride), and ethers (e.g., diethyl ether). However, one of the advantages of the process of the invention is that effective phase separation is accomplished in the absence of any added solvent. This reduces the processing costs involved in recovering and recycling solvent and also permits a food-grade product to be more readily prepared.

Once phase separation has occurred, the upper organic layer containing the deprotected alkoxylated polyol is separated from the lower aqueous layer by any method known in the art. For example, the lower aqueous layer may be drained away through either a siphon tube or bottom outlet affixed to the vessel in which the neutralization is performed. The upper organic layer remains in the vessel and may be subjected to further processing if desired.

Depending upon the composition of the deprotected alkoxylated polyol and the initial protected alkoxylated polyol, as well as the hydrolysis and neutralization conditions employed, the upper organic layer may contain minor amounts of neutralization salts, water, and aldehyde or ketone derived from the ketal protective functionality. If present, these impurities may be removed from the deprotected alkoxylated polyol product by any appropriate method. For example, the upper organic layer may be combined with an absorbent such as magnesium silicate and heated at atmospheric or reduced pressure to remove residual water and aldehyde or ketone by distillation. Once all volatile materials are removed, the remaining product is filtered to remove the absorbent containing any residual neutralization salts which may have been present. Alternatively, however, the residual water, aldehyde/ketone, and salts may be left in the deprotected alkoxylated polyol and the product used directly in a subsequent esterification step. For example, if direct esterification using a fatty acid is contemplated, the water and the aldehyde or ketone may be removed by distillation at the same time as the water generated during the esterification. Any residual salts may generally be removed by filtration of the esterified alkoxylated polyol once esterification and stripping are completed.

The deprotected alkoxylated polyol obtained by the process of this invention may subsequently be esterified by reacting with a fatty acid compound selected from the group consisting of free fatty acids, fatty acid esters, and fatty acid halides. The esterification will yield an esterified alkoxylated polyol having at least one ester group bonded directly to the polyol residue. As discussed hereinabove, such compounds are useful as low calorie fat mimetics having reduced tendency to promote anal leakage and shortened bowel transit times.

The fatty acid compound may preferably be a fatty acid or fatty acid ester having the general structure

wherein R is a $C_{11}$–$C_{23}$ olefinic or paraffinic hydrocarbon radical and $R_1$ is hydrogen or a $C_1$–$C_6$ hydrocarbon radical. Examples of suitable fatty acids include, but are not limited to, caprylic, capric, lauric, myristic, myristoleic, stearic, palmitic, palmitoleic, rincinoleic, linoleic, linolenic, elaeostearic, arachidic, arachidonic, behenic, erucic, oleic, and heptadeconoic acid. The fatty acids may be derived synthetically or from natural sources such as triglyceride lipids. Exemplary fatty acid esters include the methyl, ethyl, propyl, and isopropyl esters of the foregoing fatty acids. Mixtures of fatty acid compounds, such as the mixtures of fatty acids typically obtained by hydrolysis of a triglyceride such as corn oil or soybean oil, may be used.

Fatty acid halides which may be used in the process of this invention can have the general structure

wherein R is a $C_{11}$–$C_{23}$ olefinic or paraffinic hydrocarbon radical and X is halide, preferably chloride or bromide.

The deprotected alkoxylated polyol and the fatty acid compound are reacted for a time and at a temperature sufficient to accomplish substantially complete (i.e., greater than 90%) esterification of the hydroxyl groups of the deprotected alkoxylated polyol. The optimum reaction conditions will vary somewhat depending upon the particular type of fatty acid compound used. If a fatty acid or fatty acid ester is utilized, the reaction temperature is preferably from about 100° C. to 350° C.; reaction times of from about 1 to 48 hours are generally sufficient to accomplish substantially complete esterification of the hydroxyl groups. A coproduct having the structure HOR' (i.e., water or an alcohol) will be generated as the esterification proceeds. To drive the reaction to completion, it is desirable to remove the co-product from the reaction mixture as it forms by a suitable method such as distillation or vacuum stripping. As is well known in the art, a catalyst may be employed if desired to shorten the reaction time required. If the fatty acid compound is a free fatty acid, the catalyst is preferably an acidic catalyst. If a fatty acid ester is used, an acidic or basic catalyst may be present during esterification. When the fatty acid compound is a fatty acid halide, somewhat lower reaction temperatures (e.g., about 25° C. to 125° C.) are sufficient, particularly if a tertiary amine such as triethylamine is additionally present to take up the hydrogen halide generated during the esterification reaction. Reaction times of from about 1 to 48 hours are typically sufficient.

To accomplish substantially complete esterification of the protected alkoxylated polyol, at least about 1 (more preferably, at least about 1.1) equivalent of the fatty acid compound per equivalent of hydroxyl groups in the deprotected alkoxylated polyol is used. For reasons of economy, it is preferred to react not more than about 3 equivalents of fatty acid compound per equivalent of hydroxyl groups. Any excess fatty acid compound may be removed from the esterified alkoxylated polyol product by an appropriate method such as vacuum steam stripping.

Without further elaboration, it is believed that one skilled in the art can, using the preceding description, utilize the present invention to its fullest extent. The following examples, therefore, are to be considered as merely illustrative and not limitative of the claims or remainder of the disclosure in any way whatsoever.

EXAMPLE 1

This example demonstrates the alkoxylation of a polyol containing a ketal protective functionality. A mixture of 1,2-isopropylidene glycerin (548 parts; prepared by the procedure described in *Org. Syn.*, Coll. Vol. 3, p. 502) and potassium hydroxide (10 parts) was heated at 100° C. under reduced pressure until water evolution ceased. After combining with additional 1,2-isopropylidene glycerin (788 parts), propylene oxide (475 parts) was added at 95° C. on a pressure demand basis. After addition of the propylene oxide was completed, the protected alkoxylated polyol obtained was purged with nitrogen and then heated at 90° C. for two hours with magnesium silicate (150 parts) to remove the residual potassium catalyst. The product obtained after filtration had the following structure:

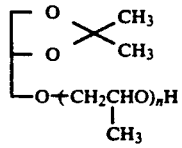

wherein n was approximately 8.1 on average.

EXAMPLE 2

This example illustrates the preparation of a deprotected alkoxylated polyol using the process of this invention. The protected alkoxylated polyol from Example 1 (1964 parts) was stirred with 0.4 N aqueous sulfuric acid (1990 parts) at room temperature for 10 minutes. During that time, the mixture became homogeneous. After 15 minutes, no isopropylidene resonances were observable by :HNMR spectroscopy. The presence of acetone in the reaction mixture was detected, however. Sodium hydroxide (ca. 50% aqueous solution) was added to the mixture with stirring until the mixture was no longer acidic. Phase separation was observed during the addition of the sodium hydroxide. This phase separation was unexpected in view of the high water solubility of a polypropylene glycol triol (e.g., propoxylated glycerin) of comparable molecular weight. The upper organic phase was separated from the lower aqueous phase and heated with magnesium silicate (ca.1 wt. %) at 100° C. while residual water (ca. 200 parts) was removed overhead. Filtration of the treated organic phase yielded a deprotected alkoxylated polyol having the general structure:

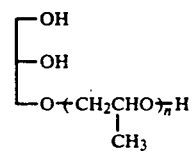

wherein n was approximately 8.1 on average.

To demonstrate the near complete recovery of the desired deprotected alkoxylated polyol in the upper organic phase, the lower aqueous phase was extracted with chloroform to yield 31 parts (only 1.7% of the theoretical yield) of the deprotected alkoxylated polyol. The effectiveness of the phase separation obtained was unexpected in view of the high water solubility of propoxylated glycerin having a similar molecular weight.

EXAMPLE 3

The esterification of a deprotected alkoxylated polyol is demonstrated by this example. The product from Example 2 (1100 parts) was heated at 240° C. with soybean fatty acids (2145 parts; 30% molar excess) under a nitrogen purge. After 6 hours, over 95 percent conversion of the deprotected alkoxylated polyol was measured by liquid chromatography (silica gel/ethyl acetate). Excess fatty acid was removed by vacuum steam stripping at 240° C. (1 mm pressure). The esterified alkoxylated polyol produced resembled refined soybean oil in appearance, odor, and taste and had the general structure:

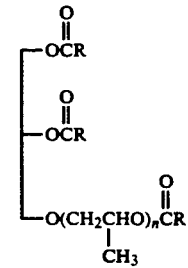

wherein n was approximately 8.1 on average and

was a fatty acid ester group derived from the soybean fatty acids.

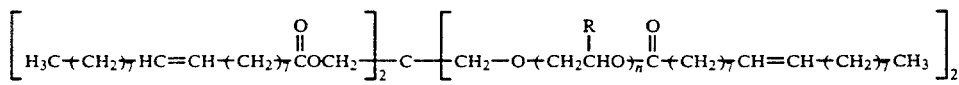

EXAMPLE 4

This example demonstrates the preparation of an esterified alkoxylated polyol using the process of the invention wherein the polyol is pentaerythritol and the alkoxylation epoxide is a mixture of 1,2-butene oxide and propylene oxide.

1,3-Dioxane-5,5-dimethanol (150 g; 1.0 mole; prepared by reacting pentaerythritol with paraformaldehyde in the presence of p-toluene sulfonic acid in accordance with the teachings of DE 3,021,983) and sodium methoxide (16.2 g of a 25% methanol solution) are heated at 75° C. under reduced pressure until methanol evolution ceases. A mixture of 1,2-butene oxide (144.2 g; 2 moles) and propylene oxide (580 g; 10 mole) is then added at 90° C. over a 6 hour period. After addition is completed, heating of the mixture is continued at 110° until substantially all of the epoxide is removed. The protected alkoxylated polyol thus obtained (ca. 874 g) has the following structure:

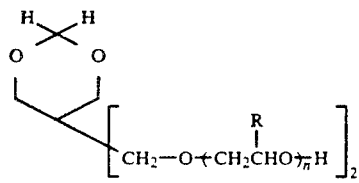

wherein n is approximately 6 on average and R is either methyl or ethyl (the molar ratio of methyl:ethyl being about 5:1).

The protected alkoxylated polyol (still containing the residual sodium catalyst) is then combined with 1.0 N hydrochloric acid (300 g) and stirred at 75° C. for 1 hour. After cooling the mixture to ca. 25° C., aqueous potassium hydroxide (1.0 N) is added slowly to the mixture with stirring until the mixture has a pH of ca. 7 (approximately 275 mL of 1.0 N potassium hydroxide will be required). After two distinct phases form, the upper organic phase is separated from the lower aqueous phase and purified as described in Example 2. The deprotected alkoxylated polyol thus obtained has the structure:

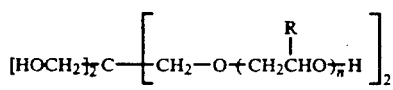

wherein n is approximately 6 on average and R is either methyl or ethyl (the molar ratio of methyl:ethyl being about 5:1).

To form an esterified alkoxylated polyol, the deprotected alkoxylated polyol is reacted with methyl oleate (1423.2 g; 4.8 mole) and potassium methoxide catalyst (45 g) for 3 hours at 150° C. while removing methanol continuously. The product is purified by heating with magnesium silicate (180 g) for 2 hours at 100° C., filtering, and then removing the excess methyl oleate by vacuum steam stripping. The structure of the esterified alkoxylated polyol is as follows:

wherein n is approximately 6 on average and R is either methyl or ethyl (the molar ratio of methyl:ethyl being about 5:1).

EXAMPLE 5

This example demonstrates the use of a protected alkoxylated polyol in the process of this invention wherein the ketal protective functionality is a tetrahydropyranyl group and the polyol is 1,3-butanediol.

The tetrahydropyranyl ether of 1,3-butanediol [174 g; 1.0 mole; prepared by reacting 3,4-dihydro-2H-pyran with 1,3-butanediol in the presence of hydrochloric acid in accordance with the teachings of Nouguier, Tet. Lett. 23(29), 2951 (1982)] and potassium hydride (4.6 g of a 35% dispersion in mineral spirits) are heated at 50° C. until hydrogen evolution ceases. The mixture is then heated to 110° C. and a mixture of 1,2-hexane oxide (500.8 g; 5 moles) and ethylene oxide [440 g; 1 mole]is added incrementally over an 8 hour period. The mixture is further heated at 110° C. until substantially all of the epoxide has reacted. A protected alkoxylated polyol having the following structure is obtained:

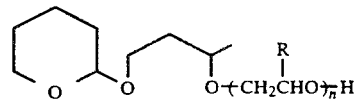

wherein n is about 6 on average and R is either hydrogen or n-butyl (the molar ratio of hydrogen:n-butyl being about 1:5).

The protected alkoxylated polyol (still containing the residual potassium catalyst) is then combined with 0.5 N phosphoric acid (500 mL) and stirred at 40° C. for 5 minutes. Aqueous ammonium hydroxide (14.8M) is added slowly to the mixture with stirring until the mixture has a pH of ca. 7 (approximately 14.2 mL of the concentrated ammonium hydroxide will be required). After two distinct phases form, the upper organic phase is separated from the lower aqueous phase and purified as in Example 2. The deprotected alkoxylated polyol thus obtained has the structure:

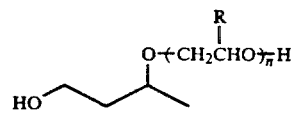

wherein n is about 6 on average and R is either hydrogen or n-butyl (the molar ratio of hydrogen:n-butyl being about 1:5).

A solution of redistilled stearoyl chloride (666.4 g; 2.2 moles) in dry chloroform (500 mL) is added drywise to a stirred solution of the deprotected alkoxylated polyol (1 mole) in a mixture of dry chloroform (2000 mL) and dry pyridine (174 g; 2.2 mole). The addition is made at room temperature under an atmosphere of dry nitrogen. After addition is completed, stirring is continued for another 24 hours. The reaction mixture is then added to water (2500 mL) and extracted several times with petroleum ether (3×1000 mL). The combined organic phases are then washed with water (2×1000 mL), dilute aqueous HCl (2×1000 mL), water (2×1000 mL), aqueous potassium bicarbonate (2×1000) and then water again (2×1000 mL). The solvent is removed by distillation under vacuum and the crude product thus obtained subjected to vacuum steam stripping to remove any residual free fatty acid. The esterified alkoxylated polyol produced has the structure:

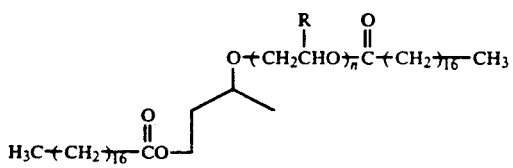

wherein n is about 6 on average and R is either hydrogen or n-butyl (the molar ratio of hydrogen:n-butyl being about 1:5).

EXAMPLE 6

This example illustrates the preparation of an esterified alkoxylated polyol using the process of the invention wherein the polyol is 1,2,6-hexanetriol and the alkoxylation epoxide is a mixture of ethylene oxide and propylene oxide.

2,2-Dimethyl-1,3-dioxolane-4-butan-4-ol (174 g; 1.0 mole; prepared by reacting 1,2,6-hexanetriol and acetone in accordance with the procedure of Example 2 of U.S. Pat. No. 4,581,470) and sodium metal dispersion (2.9 g of a 40% dispersion in mineral spirits) are heated at 50° C. until a homogeneous mixture is obtained. Ethylene oxide (44 g; 1.0 mole) is added over 1 hour at 100° C. Two hours after ethylene oxide addition is completed, the temperature is increased to 120° C. and propylene oxide (522 g; 9.0 mole) is added over 4 hours. Heating of the mixture is continued until all of the epoxide is reacted, yielding a protected alkoxylated polyol having the structure

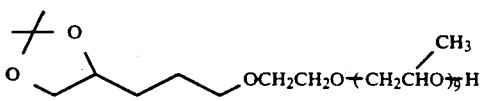

The protected alkoxylated polyol (still containing the residual sodium catalyst) is then combined with 0.25 N aqueous nitric acid (600 mL) and stirred at 20° C. for 45 minutes. Potassium hydroxide (dissolved in a minimum amount of water) is added slowly to the mixture with stirring until the mixture has a pH of ca. 7 (approximately 5.6 g potassium hydroxide will be required). After two distinct phases form, the upper organic phase is separated from the lower aqueous phase and used without further purification in the subsequent esterification step. The structure of the deprotected alkoxylated polyol is

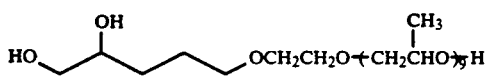

The deprotected alkoxylated polyol is esterified with a 20% molar excess of coconut fatty acid (Emery 621 grade, available from the Emery Group of Henkel Corporation) by heating to 240° C. under a nitrogen purge.

The residual acetone and water from the hydrolysis step as well as the water generated during the esterification reaction are removed during this process. After attaining a hydroxyl conversion of over 95%, the unreacted fatty acid is removed by vacuum steam stripping at 1 mm and 240° C. Residual salts are removed by filtration through a bed of diatomaceous earth. The esterified alkoxylated product obtained in this manner has the structure:

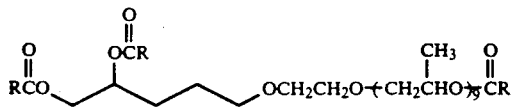

wherein the

groups are fatty acid ester groups derived from the coconut fatty acid.

I claim:

1. A process for producing a deprotected alkoxylated polyol comprising the steps of
   (a) contacting an admixture of water and a protected alkoxylated polyol having a ketal protective functionality with a catalytically effective amount of an acid under conditions effective to hydrolyze the ketal protective functionality thereby forming a deprotected alkoxylated polyol;
   (b) adding a base to the admixture so as to neutralize the acid and to cause the admixture to form a first and second phase in the absence of a water-immiscible organic solvent wherein the water is predominantly contained in said first phase and the deprotected alkoxylated polyol is predominantly contained in said second phase; and
   (c) separating the second phase containing the desired deprotected alkoxylated polyol from the first phase.

2. The process of claim 1 wherein the ketal protective functionality has the general structure

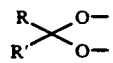

wherein R and R' are the same or different and are independently selected from the group consisting of hydrogen, alkyl, aryl, and aralkyl.

3. The process of claim 1 wherein the protected alkoxylated polyol is a protected propoxylated polyol.

4. The process of claim 1 wherein the protected alkoxylated polyol is a protected alkoxylated glycerin.

5. The process of claim 1 wherein the acid is a mineral acid.

6. The process of claim 1 wherein the base is selected from the group consisting of alkali metal oxides, alkali metal hydroxides, alkaline earth oxides, alkaline earth hydroxides, and mixtures thereof.

7. A process of producing a deprotected propoxylated glycerol comprising the steps of
   (a) contacting an admixture of water and a protected propoxylated glycerol having a cyclic ketal protective functionality with a catalytically effective amount of a mineral acid at a temperature of from about 10° C. to 75° C. for a time effective to hydrolyze the cyclic ketal protective functionality thereby forming a deprotected propoxylated glycerol;

(b) adding an alkali metal hydroxide to the admixture so as to neutralize the mineral acid and to cause the admixture to form a first and second phase in the absence of a water-immiscible organic solvent wherein the water is predominantly contained in said first phase and the deprotected propoxylated glycerol is predominantly contained in said second phase; and (c) separating the second phase containing the desired deprotected propoxylated glycerol from the first phase.

8. The process of claim 7 wherein the cyclic ketal protective functionality has the general structure

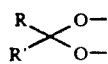

wherein R and R' are the same or different and are independently selected from the group consisting of hydrogen, alkyl, aryl, and aralkyl.

9. The process of claim 7 wherein the mineral acid is selected from the group consisting of sulfuric acid, hydrochloric acid, nitric acid, and phosphoric acid.

10. The process of claim 7 wherein the protected propoxylated glycerin has the general structure

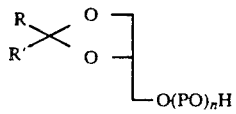

wherein R and R' are the same or different and are independently selected from the group consisting of hydrogen, methyl and ethyl, PO is an oxypropylene unit, and n is from about 2 to 15 on average.

11. The process of claim 7 wherein R and R' are each methyl.

12. The process of claim 7 wherein the weight ratio of water to protected propoxylated glycerin is from about 0.1:1 to about 2:1.

13. The process of claim 7 wherein the contact time in step (a) is from about 1 to 90 minutes.

14. A process for producing an esterified alkoxylated polyol comprising the steps of (a) reacting a protected polyol having at least one free hydroxyl group and a ketal protective functionality with an epoxide in the presence of a catalytically effective amount of a basic alkoxylation catalyst under conditions effective to form a protected alkoxylated polyol wherein the ketal protective functionality remains intact;

(b) contacting an admixture of the protected alkoxylated polyol and water with a catalytically effective amount of an acid under conditions effective to hydrolyze the ketal protective functionality thereby forming a deprotected alkoxylated polyol;

(c) adding a base to the admixture so as to neutralize the acid and to cause the admixture to form a first and second phase in the absence of a water-immiscible organic solvent wherein the water is predominantly contained in said phase and the protected alkoxylated polyol is predominantly contained in said second phase;

(d) separating the second phase containing the deprotected alkoxylated polyol from the first phase;

(e) reacting the deprotected alkoxylated polyol with a fatty acid moiety selected from the group consisting of free fatty acids, fatty acid esters, and fatty acid halides to form the desired esterified alkoxylated polyol.

15. The process of claim 14 wherein the protected polyol is derived from a polyol selected from the group consisting of glycerin, trimethylolpropane, trimethylolethane, 1,2,6-hexanetriol, pentaerythritol, sugar alcohols, and sugars.

16. The process of claim 14 wherein the epoxide is a $C_3-C_6$ aliphatic epoxide.

17. The process of claim 14 wherein the ketal protective functionality has the general structure

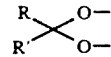

wherein R and R' are the same or different and are independently selected from the group consisting of hydrogen, alkyl, aryl, and aralkyl.

18. The process of claim 14 wherein the acid is a mineral acid.

19. The process of claim 14 wherein the base is selected from the group consisting of alkali metal oxides, alkali metal hydroxides, alkaline earth oxides, alkaline earth hydroxides, and mixtures thereof.

20. The process of claim 14 wherein step (b) is carried out at a temperature of from about 10° C. to 75° C.

* * * * *